United States Patent [19]

Jones et al.

[11] Patent Number: 5,157,601

[45] Date of Patent: Oct. 20, 1992

[54] METHOD FOR ESTIMATING BODY ALCOHOL CONCENTRATION

[75] Inventors: Thomas P. Jones, Gwent; Paul M. Williams, Powys, both of Great Britain

[73] Assignee: Alcolator Limited, South Glamorgan, Great Britain

[21] Appl. No.: 461,644

[22] Filed: Jan. 5, 1990

Related U.S. Application Data

[60] Continuation-in-part of Ser. No. 262,125, Oct. 25, 1988, abandoned, which is a division of Ser. No. 878,864, May 20, 1986, abandoned.

[30] Foreign Application Priority Data

Oct. 4, 1984 [GB] United Kingdom .................. 8425089
Jul. 30, 1985 [GB] United Kingdom .................. 8519155
Sep. 23, 1985 [GB] United Kingdom PCT/GB85/00438

[51] Int. Cl.⁵ ............................................ G06F 15/42
[52] U.S. Cl. ......................... 364/413.11; 364/413.01; 364/413.29
[58] Field of Search ............. 364/413.01, 413.11, 364/413.29; 128/719; 436/900, 901

[56] References Cited

U.S. PATENT DOCUMENTS

| | | | |
|---|---|---|---|
| 3,668,866 | 6/1972 | Lund | 368/10 |
| 4,192,000 | 3/1980 | Lipsey | 364/413.29 |
| 4,380,802 | 4/1983 | Segar et al. | 364/413.29 |
| 4,475,901 | 10/1984 | Kraegan et al. | 604/67 |
| 4,507,744 | 3/1985 | McFiggans et al. | 364/708 |
| 4,575,804 | 3/1986 | Ratcliff | 364/709.03 |
| 4,592,443 | 6/1986 | Simon | 73/23.3 |
| 4,686,624 | 8/1987 | Blum et al. | 364/413.29 |
| 4,7697,539 | 1/1989 | Forest | 235/85 R |

FOREIGN PATENT DOCUMENTS

| | | | |
|---|---|---|---|
| 0143411 | 6/1985 | European Pat. Off. | 364/413.01 |
| 3233829 | 3/1984 | Fed. Rep. of Germany | 364/413.09 |

OTHER PUBLICATIONS

"Alco-Calculator: An Educational Instrument", sales brochure, Datatizer Slide Charts, Inc., 1972.
*Alcohol, Drugs and Road Traffic*, Cooper et al., Juta & Company Limited, pp. 82-146.
"Alcohol Determination—Some Physiological and Metabolic Considerations", Dubowski, presented at National Conf. on Alcohol and Traffic Safety, Pittsburgh, PA, 1961, pp. 91-97.
"Effects of Alcohol Intake on Subjective and Objective Variables Over Five-Hour Period", Ekman et al.
*Drink, Drugs and Driving,* Walls et al., 1985, pp. 9-21.
"Factors Affecting the Absorption Rate of Alcohol into the Blood—A Pilot Study", 1981, Cameron, New South Wales Police Department Breath Analysis Section, pp. 1099-1110.
"Proceedings: Seventh International Conference on Alcohol, Drugs and Traffic Safety", Melbourne 23-28, 1977, Australian Government Publishing Service, pp. 200-205.
"Temporal relations between blood alcohol concentration and alcohol effect: an experiment with human subjects", Radlow et al., *Psychopharmacy*, Springer-Verlag, 1985, pp. 260-266.
"Alcohol and the Motorist", Bicknell, 1960, London, pp. 1-4.
"Absorption, Distribution and Elimination of Alcohol: Highway Safety Aspect," Dubowski et al., *J. Studies on Alcohol,* Supp. No. 10, Jul. 1985, pp. 98-108.
Intoxication Test Evidence: Criminal and Civil, Fritzgerald et al., 1987, The Lawyers Co-Operative Publishing Co., pp. 62-120.
"Variability in Blood Alcohol Concentrations", O'Neill et al., *J. of Studies on Alcohol,* vol. 44, No. 2, 1983, pp. 222-230.

*Primary Examiner*—Roy N. Envall, Jr.
*Assistant Examiner*—David Huntley
*Attorney, Agent, or Firm*—Young & Thompson

[57] ABSTRACT

This invention relates to apparatus for estimating body alcohol concentration from personal body characteristics. For example, a calculator 10 has a keyboard 12 through which the user can input information concerning his sex, body weight, degree of fat, food consumption, alcohol consumption and the timing of these last two events. Depending on the mode into which the apparatus is set, the user can be told his maximum body alcohol concentration, how much more he may drink before reaching a legal limit, or when he may achieve the legal limit if he drinks no more.

10 Claims, 1 Drawing Sheet

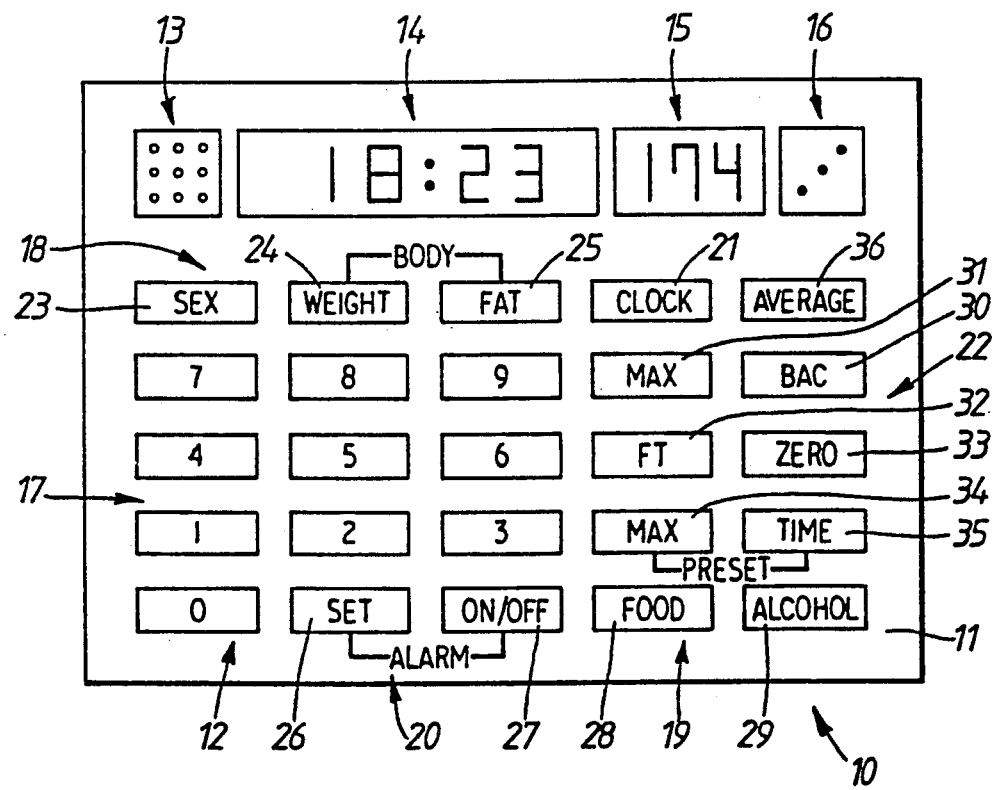

METHOD FOR ESTIMATING BODY ALCOHOL CONCENTRATION

This application is a continuation-in-part of application Ser. No. 07/262,125 filed Oct. 25, 1988, now abandoned, which is a division of application Ser. No. 06/878,864 filed May 20, 1986, now abandoned.

This invention relates to a method for limiting body alcohol concentration of a consumer.

BACKGROUND OF THE INVENTION

In the majority of countries, legislation is now in force making it an offense to be in control of a motor vehicle when the body alcohol concentration is above a certain level. This is sometimes expressed in terms of the blood/alcohol concentration or the breath/alcohol concentration. Charts have been produced intended to give drinking drivers some guide as to what alcohol consumption will keep them within the law. However, they are unable to take account of the many variables which affect the alcohol concentration in a person's body. Coin freed breath-testing machines are available in some pubs, but they are not well used and are susceptible to "mouth alcohol" and incorrect usage. Proposals to market individual breath-testers to the general public have failed because of the expense of the units and the difficulty of ensuring that they are used exactly in accordance with the manufacturers' instructions.

SUMMARY OF THE INVENTION

It is the object of the invention to produce a method which will enable a drinker to satisfactorily limit his body alcohol concentration.

From one aspect this invention consists a method for limiting the body alcohol concentration of a consumer, comprising the steps of:

(a) determing the body characteristics of the consumer;

(b) measuring the weight of the alcohol consumed (Ac) by the consumer;

(c) measuring the time elapsed (T) during alcohol consumption;

(d) calculating the estimated body alcohol concentration (C) as a function of the body characteristics, weight of alcohol consumed, time of consumption and (e) correcting said calculated concentration (C) according to whether food consumption (F) comprises (1) none, (2) a snack, or (3) a full meal, so as to obtain a corrected body alcohol concentration (Cc) by multiplying C by 1.0 if no food is consumed; by about 0.9 for a snack and by about 0.7 for a full meal; and (f) the consumer altering at least one of (Ac), (T) and (F) to ,maintain (Cc) below a predetermined maximum.

BRIEF DESCRIPTION OF THE DRAWING

The invention may be performed in various ways and a specific embodiment, by way of example, will now be described with reference to the accompanying drawing which is a plan view of an alcohol body concentration calculator.

DETAILED DESCRIPTION OF THE INVENTION

The calculator, which is generally indicated at 10, has a body 11 containing the computing and interface circuits (not shown) together with a battery. It also includes a clock.

Mounted in the front face of the body is a keyboard 12, a buzzer or alarm 13, a four digit numerical display 14, a three digit numerical display 15 and a dot matrix display 16.

The keyboard 12 incorporates a number of groups of keys: a numeric group generally indicated at 17, personal body characteristic keys generally indicated at 18, consumption keys generally indicated at 19, alarm control keys generally indicated at 20, a clock control key 21 and data identification and request keys generally indicated at 22.

In addition to these keys there are three controls on the rear panel of the calculator. These are a reset key which clears an information inputed using the body characteristic keys 18 or the consumption keys 19, but does not affect the clock function and a time reset key which clears the clock and the consumption data, but does not alter the body characteristics data. Finally there is a multi-position switch on the rear panel which adjusts the units of the data displayed on display 15 in accordance with the country in which the calculator is to be used.

The calculator is used in the following manner. The user first informs the calculator of his or her general body characteristics by using the keys 18. The user first inputs their sex by pressing sex key 23 followed by a code entry, 0 for male or 1 for female. Similarly their weight is fed in by pressing weight button 24 and either the subject's actual body weight or a coded weight within various set ranges. An estimate of the user's body fat is generally notified by pressing the fat key 25 followed by either 0 for fatty, 1 for normal or 2 for little fat. Alternatively and preferably the user may input his body weight and height from which build factor B can be calculated. This information is held permanently in a memory of the calculator unless the reset key mentioned above is pressed.

Having set the calculator 10 for his personal use the user then sets the clock to the correct time by pressing the time/reset key on the rear panel, typing the real time plus one minute on the numeric keys 17 and pressing clock button 21 to start the timer when the display time equals the real time. He can also program the alarm by pressing set button 26, typing in the alarm time, which will be displayed on display 14 and then pressing the set button 26 again to return the display to the clock. The on/off switch 27 is used to enable or disable the alarm to function.

The user then carries the calculator 10 with him and when he is about to consume either food or alcohol he presses the respective one of consumption buttons 19 (food button 28 and alcohol button 29) and types in the starting time of the intake. This appears on display 14. He then either types in a code for the type of meal (e.g. 0—light snack, 1—light meal, 2—full meal) or the quantity of alcohol he is about to drink in accordance with a code provided. When he has completed the meal or drink he types the appropriate consumption button followed by the time followed by the consumption button again. Alternatively in either case the beginning and end times may be logged automatically by the mere pressing of the appropriate consumption button. In the event of a failure to type in an end time for either type of consumption the calculator may assume a certain consumption time, e.g. light snack—quarter of an hour or one pint—half an hour.

Preferably the consumption information is fed in as the consumption occurs, but the calculator can be arranged to accept it retrospectively. Provided with this information and the body characteristic data the calculator can work put as explained below an estimate of the body alcohol concentration of the user. This can be displayed on display 15 simply by pressing the blood alcohol concentration button 30. Simultaneously the display 16 will show a rising or falling line depending on whether the concentration is rising or falling. A horizontal line indicates a constant level.

The user may be interested to know when the concentration will or has reached a maximum and this can be obtained by pressing MAX key 31 which will display the preceding or succeeding concentration maximum on display 16 and indicate a trend with a rising, falling or constant line on display 16. Thus if the concentration has already peaked the value will be followed by a descending line, but if the maximum has not yet been reached the line will be ascending.

Alternatively the user may wish to know what his concentration will be at a future time, e.g. when he wishes to leave a party. This can be obtained by pressing forecast time button 32 and then typing in the future time which will appear on display 14. The user then presses blood alcohol concentration button 30 and the concentration at the selected time will be displayed on display 15. This value can be cleared by pushing button 32 again.

Another function is provided by zero button 33 which when depressed displays the time, on display 14, at which the concentration will be reduced to zero.

The user may wish to set himself a maximum concentration. This can be done by pushing PRESET MAX key 34, entering on display 15 the limit preferred and repressing key 34. If the consumption data at any time indicates the limit will be exceeded the alarm buzzer 13 sounds. The function can be cleared by pressing key 34 twice, otherwise the preset maximum is stored permanently.

An indication of the maximum number of drinks which can yet be taken before the preset max setting is exceeded can be obtained by pressing PRESET TIME button 35 and typing in the time at which drinking will finish. The number of drink units still available is then displayed on display 15.

Finally an average weekly consumption can be displayed on display 15 by depressing average button 36.

Thus it will be seen that the calculator 10 not only provides an estimate of the instantaneous alcohol concentration but also can inform the user of the trend of that concentration and what will be its status in the future. In this way the drinker can plan his consumption so that he either stays within the limits or so that his concentration will have fallen to an acceptable level when he next has to drive a car.

In this sense it is considerably more versatile than a breath-testing apparatus which only gives an instantaneous value without any indication of a trend. It also eliminates the need for replaceable mouth tubes and expert monitoring of its use.

For a long time the calculation of blood alcohol concentration has been based on the Widmark equation which only takes into account the alcohol ingested subject's body weight and a factor which is covered by the sex of the subject. In practice the equation provides an inadequate approximation.

It has now been determined that the blood alcohol concentration at any given time can be much more precisely estimated by taking into account other factors. These are essentially the quantity of water contained in the user's body, the alcohol lost by burning within the body due to the elapse of time, and the effect of food on alcohol absorption. These factors can be used in accordance with the calculation set out below.

The personal details of the user should, in the majority of cases, be relatively constant—or at least constant enough not to have to enter them into the calculator on each occasion it is called upon to produce a reading.

The three fixed personal factors will tell the computer how much water the user's body has and so which is available to dilute the alcohol entering the general body system.

A. Body Weight (W)—self explanatory. Note, however, that it is essential to make use of kilograms, not stones and pounds.

B. Sex (Widmark) Factor (S)—not all the body weight is water but, in general, men have a higher proportion of water in their bodies than do women. This factor is multiplied by the body weight to arrive at a value for the quantity of water in that person's body if he was of average build. The Widmark feature does, as the name suggests feature in the basic Widmark equation.

C. Build Factor (B)—this makes allowances for those who are not of average build. Obese persons have a higher fat:water ratio than normal people. Muscle is composed of much water so that, for instance, an athlete will have a higher water:fat ratio than a normal person and so will be able to dilute more extensively the alcohol taken by him.

Thus, the personal factor (P) is given by the formula:

$$P = W \times S \times B \qquad \text{equation 1}$$

and will be, essentially, the weight of water in the particular person's body.

As has been said, this should remain constant for that person and could, therefore, be held permanently in memory—or at least until such time as it was purposefully amended. Preferably, it should not need to be entered each time the device is used.

The next two factors relate to how much alcohol is actually present in the body, in toto, at any particular time. It does not infer that all this alcohol is necessarily in the bloodstream, some of it may still be in the gut and thereby be unable to contribute to the blood or breath alcohol concentrations at that point in time. It is governed by two factors:

D. Alcohol Consumed (Ac)—measured in grams. In bars where alcohol is sold by way of trade beers are sold by multiples of ½ pint, spirits of 1/6 gill and wine by the standard glass. Each such volume, known as a 'drink unit', will contain about the same quantity of alcohol although it may prove necessary on the device to make allowances for out of the ordinary beers of high alcohol content, and also for some spirits, such as Polish Vodka.

In general, however, by knowing the number of drink units taken it is possible to calculate the net weight of alcohol ingested. This is given the Value 'D'.

E. Alcohol Lost (Al)—also measured in grams. Once alcohol starts to enter the blood (and this happens fairly quickly after consumption has got under way) the liver will start to burn it up. However, this organ can only deal with so much alcohol at a time and it quickly becomes saturated. Above about 15–20 mg% of alcohol in the blood the liver works flat out and increasing the alcohol content in the blood makes no difference to the elimination rate.

However, a bigger liver can burn up more alcohol in a particular time but, since the body is bigger anyway, there is no actual difference made to the rate of decrease in the blood alcohol concentration. That remains fairly constant and is unaffected by body weight. It is, therefore, necessary to take into account the body weight (W) of the person and the time in hours (T) since consumption commenced up until the time is required to get an estimate of the then current blood alcohol concentration.

The weight of alcohol (Al) burnt up in the liver is given by the formula:

$$Al = 0.1 \times T \times W \qquad \text{equation 2}$$

F. Alcohol Present (Ap)—also measured in grams. Thus, the weight of alcohol present in the body at any particular time is given by the expression:

$$Ap = Ac - Al \qquad \text{equation 3}$$

G. Alcohol Dilution

Quite simply the amount of alcohol given by Ap spreads itself through the water given by the value 'P' (equation 1) so that the concentration (C) arrived at will be given by:

$$C = \frac{Ap}{P} \qquad \text{equation 4}$$

Food Effects

This value of 'C' derived from equation 4 will be the blood alcohol concentration if the drink was consumed on an empty stomach. If a snack was taken just prior or contemporaneous to the alcohol then the value of 'C' must be reduced in order to arrive at a more realistic blood alcohol level If a full meal has been taken then even more of a reduction must be made. The final expression is given by the formula:

$$Cc = C \times F$$

where Cc is the current concentration of alcohol in the blood

C is the value calculated from equation 4 and F is a 'food factor'.

So, if the stomach was empty the value of F will be unity. F will decrease to some extent with the ingestion of food, the heavier the meal the greater the decrease. However, since the food will itself be digested and absorbed, it is necessary to apply a time correction to F so that, after about 3-4 hours, it will return again to unity—corresponding to the emptying of the gut of food.

It may prove necessary to make allowances not just for the quantity of food taken, and when, but also for the nature of the food. For instance, meals heavy in fat are absorbed more slowly than those high in carbohydrate content so that it may be necessary to adjust, accordingly, the rate at which F returns to unity after having been decreased on account of a quantity of food taken.

In addition to apparatus for straight forward estimating for blood alcohol concentration the invention also includes apparatus for playing a game utilising the basic apparatus. Thus a user can act out various drinking patterns by punching in different intakes, different timings and different food consumption to mimic a night in a pub, at a disco or at a dinner party etc. and the game will then display for him the consequences of that drinking if he decides to drive home or drive the next morning etc. etc. The apparatus would in that case almost certainly include indication means to allow for the input of date and a graphic display which will produce graphics in accordance with the time elapsed in the game and the estimated alcohol concentration Cc at that time.

One method of calculating the estimated alcohol concentration Cc is set out in the following computer program which also allows alcohol consumption required to reach a particular body alcohol concentration Cc to be reached. The program is written in Basic and for programming convenience different abbreviations are given to those set out above. However a detailed list of variables follows the program listing as does an explanation of the various lines of the program:

PROGRAM

```
20 SCNCLR
30 IF WF=0 THEN GOTO 70
40 INPUT "⏎⏎NEW USER (Y/N)= ";I$
50 IF I$="N" THEN GOTO 320
60 IF I$<>"Y" THEN GOTO 40
70 CLR
80 INPUT "⏎⏎SEX <M/F>= ";S$
90 IF S$="M" THEN Z=1.340:YY=12.469:GOTO 120
100 IF S$="F" THEN Z=1.371:YY=3.467:GOTO 120
110 IF S$<>"F" THEN PRINT "⏎M OR F PLEASE!":GOSUB 910:GOTO 80
120 INPUT "⏎⏎YOUR BODY WEIGHT <KG>= ";W%
130 IF W%<35 THEN PRINT "⏎⏎TOO LIGHT!":GOSUB 910:GOTO 120
140 IF W%>120 THEN PRINT "⏎⏎TOO HEAVY!":GOSUB 910:GOTO 120
150 INPUT "⏎⏎YOUR HEIGHT <CM>= ";HCM%:H=HCM%/100
160 IF HCM%<135 THEN PRINT "⏎⏎TOO SHORT!":GOSUB 910:GOTO 150
170 IF HCM%>200 THEN PRINT "⏎⏎TOO TALL!":GOSUB 910:GOTO 150
180 BMI=W%/H^2:REM BODY MASS INDEX
190 FPBW=(2*BMI)-YY:REM FAT PERCENT BODYWEIGH
200 TBW=0.724*(W%-(FPBW/100*W%)):REM TOTAL BODY WATER
210 WF=TBW/(W%*0.8):REM 0.8=WATER RATIO FOR BLOOD:WF=WIDMARK FACTOR
220 IF WF<0.5 OR WF>0.85 THEN PRINT "⏎BODY OUT OF PROPORTION!":GOSUB
    910:GOTO 70
230 INPUT "⏎⏎YOUR AGE <YRS>= ";Y%
240 IF Y%<15 THEN PRINT "⏎⏎TOO YOUNG!":GOSUB 910:GOTO 230
250 IF Y%>99 THEN PRINT "⏎⏎TOO OLD!":GOSUB910:GOTO 230
260 IF Y%>50 THEN Y%=50
```

PROGRAM continued

```
270 Y=Y%-14:U=0.094-(Y/2000):IF U>0.095 THEN U=0.095
280 INPUT "]]REGULAR DRINKER <Y/N>= ";E$
290 IF E$="Y" THEN 320
300 IF E$="N" THEN U=U-0.015:GOTO 320
310 PRINT "]]Y OR N PLEASE!":GOSUB 910:GOTO 280
320 INPUT "]]OPTION <1 OR 2>= ";R$
330 IF R$="2" THEN 610
340 IF R$<>"1" THEN PRINT "]]1 OR 2 PLEASE!":GOSUB 910:GOTO 320
350 GOSUB 860
360 GOSUB 770
370 IF F$="N" THEN GOTO 480
380 INPUT "]]PRE-FOOD DRINKS= ";DP
390 IF DP<0 THEN GOSUB 940:GOTO 380
400 IF DP>20 THEN PRINT "]]QRTOO MANY!Q":GOSUB 910:GOTO 380
410 INPUT "]]DRINKS WITH OR AFTER FOOD= ";DA
420 IF DA<0 THEN GOSUB 940:GOTO 410
430 IF DA>20 THEN PRINT "]]QRTOO MANY!Q":GOSUB 910:GOTO 410
440 IF DA=0 AND DP=0 THEN C%=0:GOTO 560
450 IF (DA+DP)/T>12 THEN GOSUB 980:GOTO 380
460 IT=(9*DP)+(9*DA*V):IC=IT-(U*T*W%)
470 C%=IC/(W%*WF)*100:GOTO 550:END
480 INPUT "]]NUMBER OF DRINKS CONSUMED= ";D
490 IF D<0 THEN GOSUB 940:GOTO 480
500 IF D=0 THEN C%=0:GOTO 560
510 IF D>30 THEN PRINT "]]QRTOO MANY!Q":GOSUB 910:GOTO 480
520 IF D/T>12 THEN GOSUB 980:GOTO 480
530 IC=(9*D)-(U*T*W%)
540 C%=IC/(W%*WF)*100
550 IF C%<0 THEN C%=0
560 PRINT "]]QQYOUR MAXIMUM BAC IS"C%"MG/%"
570 PRINT"QQQQ]]]]]]PRESS RSPACE-BARR TO REPEAT"
580 GET F$:IF F$<>" " THEN 580
590 GOTO 20
600 END
610 GOSUB 860
620 GOSUB 770
630 INPUT "]]MAXIMUM DESIRED BAC <MG/%>= ";C%
640 IF C%<0 THEN GOSUB 940:GOTO 630
650 IF C%>200 THEN PRINT "]]QRSORRY! THAT'S TOO HIGH!Q":GOSUB
    910:GOTO 630
660 IF C%<=5 AND T<=1 THEN D%=0:GOTO 710
670 M=(W%*WF*C%):N=(M/(100*V))+(U*T*W%)
680 D=(N/9)
690 IF D<0 THEN D=0
700 IF F$<>"N" THEN D%=D-(0.1*D)+0.5:ELSE D%=D+0.5
710 PRINT "]]QQMAXIMUM DRINK CONSUMPTION=";D%;"UNIT(S)"
720 IF D%/T>12 THEN PRINT "]]QRVERY HIGH INTAKE RATE!Q"
730 PRINT"QQQQ]]]]]]PRESS RSPACE-BARR TO REPEAT"
740 GET F$:IF F$<>" " THEN 740
750 GOTO 20
760 END
770 INPUT "]]FOOD <N,S OR M>= ";F$
780 IF F$="N" THEN X=1:GOTO 820
790 IF F$="S" THEN X=0.9:GOTO 820
800 IF F$="M" THEN X=0.7:GOTO 820
810 PRINT "]]N, S OR M PLEASE!":GOSUB 910:GOTO 770
820 IF T>=2 THEN V=X+(0.05*T):ELSE V=X
830 IF V>1 THEN V=1
840 RETURN
850 END
860 INPUT "]]TIME (HOURS)= ";T
870 IF T<=0 THEN GOSUB 940:GOTO 860
880 IF T<0.25 THEN PRINT "]]TOO QUICK!":GOSUB 910:GOTO 860
890 IF T>12 THEN PRINT "]]TOO LONG!":GOSUB 910:GOTO 860
900 RETURN
910 FOR L=1 TO 700:NEXT L
920 RETURN
930 END
940 PRINT "]]DON'T BE RIDICULOUS!"
950 FOR L=1 TO 700:NEXT L
960 RETURN
970 END
980 PRINT "]]QRDRINKING TOO FAST!Q"
990 FOR L=1 TO 700:NEXT L
1000 RETURN
1010 END
```

List of Variables

In alphabetical order:

| Variable | Type | Description Function |
|---|---|---|
| BMI | Computed (numeric) | Body mass index, in kg/m², used to calculate WF. |
| C % | OPTION '1' computed OPTION '2' user input (both numeric) | Blood alcohol concentration - mg %. (max 200 mg %) |
| D | OPTION '1' user input OPTION '2' computed (both numeric) | Drinks units consumed, no food (0-30 drinks) Drinks units available, before rounding up or down. |
| DA | User input (numeric) | Drinks taken with/after food (0-20 drinks) |
| DP | User input (numeric) | Drinks taken previous to food (0-20 drinks) |
| D % | Computed (numeric) | Corrected value of 'D' for drink units available - OPTION '2'. |
| ES | User input (string) | Is the user an experienced drinker? (Yes or No). |
| FS | User input (string) | What type of food taken? (N, S or M) ie (No, snack or meal). |
| FPBW | Computed (numeric) | Fat percent body weight (unit less), used to calculate WF. |
| FFS | User input (string) | Waits for space-bar to be hit to rerun the calculation (line 580). |
| HCM % | User input (numeric) | Height of subject in cm. (135-200 cm). |
| H | Computed (numeric) | Height of subject in meters, computed from (HCM %/100). |
| IC | Computed (numeric) | Current weight of alcohol in body in grams, OPTION '1'. |
| IT | Computed (numeric) | Total weight of alcohol ingested, in grams, OPTION '1'. |
| IS | User input (string) | Is the current user a new user? (Yes or No) |
| L | Assigned (numeric) | Used only in time delay sequence |
| M | Computed (numeric) | Weight of alcohol in body, in grams, OPTION '2' |
| N | Computed (numeric) | Weight of alcohol which can be ingested, in grams, OPTION '2'. |
| RS | User input (string) | Selects option of type of calculation. (1 or 2) |
| SS | User input (string) | Sex of user. (M or F). |
| T | User input (numeric) | Time since drinking began (in hours) (0.25 to 12 hours). |
| TBW | Computed (numeric) | Total body water, in kg, used to calculate WF. |
| U | Computed (numeric) | Personal alcohol breakdown rate (in grams) alcohol/kg body weight/ hours, (max 0.095 g/kg/hour). |
| V | Computed (numeric) | Food factor (any value between 0.7 and 1.0). |
| W % | User input (numeric) | Body weight of subject in kg (35-120 kg). |
| WF | Computed (numeric) | Personal Widmark Factor (0.5-0.85) |
| X | Assigned (numeric) | Value assigned to FS, for calculation of 'V' (0.7, 0.9 or 1.0). |
| Y % | User input (numeric) | Age of subject, in years (15-99 years) |
| Y | Computed (numeric) | Age of subject minus 14 years. Used to compute 'U'. |
| YY | Assigned (numeric) | Empirical values used to calculate FPBW (line 190). (Males, YY = 12.469; Females, YY = 3.467) |
| Z | Assigned (numeric) | Empirical values used to calculate FPBW (line 190). (Males, 2 = 1.340; Females, 2 = 1.371) |

| LINE NO (s) | EXPLANATION |
|---|---|
| 30 | Checks whether the Widmark Factor (WF) is set at zero; prohibits calculation on a zero factor. |
| 40-60 | If the user is the same as last time then his personal data is still held and the re-entry stage is bypassed. A new user must enter his personal details. |
| 70 | Clears existing data from memory if the user is a new one. |
| 80-310 | Input of user personal details. These are displayed as they are input and are held until a new user comes to operate the device. |
| 80-110 | Asks the subject's sex and, based upon the answer, assigns known empirical values to the factors 'Z' and 'YY'. |
| 120-140 | Asks the subject his body weight, but allows values only between 35 and 120 kg inclusive. |
| 150-170 | Asks the subject his height, but allows values only between 135 and 200 cm; then converts answer to meters. |
| 180-210 | Calculation of personal Widmark Factor (WF), via the Body Mass Index (BMI), the Fat Percent Body Weight (FPBW) and the Total Body Water (TBW). Blood contains 80% water, hence the 0.8 factor in line 210. |
| 230-250 | Calls for subject's age, but allows values only between 15 and 99 to be used. |
| 260-270 | Calculates the factor 'U', being the weight of alcohol (per kilogram of body weight) which the subject can break down. It decreases with age up to the age of 50. The maximum allowed value of 'U' is 0.095 (g/kg/hour). |
| 280-310 | If the drinker is not a regular drinker then his breakdown rate will be a little lower. |
| 320 | Allows selection either of calculation of BAC from a known intake (OPTION '1'), or calculation of drinks allowance to arrive at a stated BAC maximum (OPTION '2'). |
| 330 | Sends the program to OPTION '2', if that route is selected by the user. |
| 350 | Goes into a sub-routine - to input the time period of drinking. |
| 360 | Goes into a sub-routine where the 'Food Factor' is calculated. |
| 370 | Bypasses the 'pre-food drinks?' and the 'with post-food drinks?' questions, if no food was taken. |
| 380-400 | Calls for number of drinks taken before food. Must be at least zero, and no more than 20. |
| 410-430 | As above, for drinks with or after food. |
| 440 | If no drinks were taken the BAC must be zero. |
| 450 | If, overall, more than 12 drinks per hour are taken this is considered too fast. |
| 460 | Calculation of IT, the grams intake of alcohol. The 'V' factor reduces the nett absorption where food has been taken. Calculation of IC, the current loading, which is the intake minus the breakdown loss. |
| 470 | Calculation of the BAC (C %) where food was taken. |
| 480-520 | Calls for drinks input where no food was taken. No more than 30 units overall, or 12 units per hour are allowed. |
| 530-540 | Calculation of the BAC where no food was taken. |
| 550 | If the drinking rate was slow then the breakdown rate is faster than absorption. This prevents a negative BAC value being calculated by the computer. |
| 560 | Result of BAC calculation. |
| 570-590 | Would probably all be replaced by at time-out sequence, eg: 570 FOR L = 1 TO 1000:NEXT L:GOTO 20 |
| 610-620 | Start of OPTION '2' calculation. Food and time factors are called for. |
| 630 | Calls for maximum desired BAC and restricts range between 0 and 200 mg %. |
| 660 | If the BAC maximum is 5 or less and the time is 1 hour or less then the subject is advised not to drink at all. |
| 670 | Calculation of N, the grams of alcohol allowed. |
| 680 | Calculation of drink units, each of which has 9 g of alcohol. |
| 690 | Drinks units allowed cannot number less than zero. |
| 700 | Answer rounded down for empty stomach, and up for a full stomach. |

-continued

| LINE NO (s) | EXPLANATION |
|---|---|
| 710 | Gives result of drinks unit allowance calculation. |
| 720 | Warns that the maximum BAC in the time stated would require a very high intake rate (more than 12 per hour). |
| 730–750 | Would be replaced by time-out sequence as lines 570–590. |
| 770–820 | Sub-routine calculates food factor 'V'. First a value of 'X' is assigned. If the time is more than 2 hours then food is absorbed so the value of 'X' is increased to arrive at 'V'. The 'N', 'S' or 'M' responses could be labelled keys (see 7.3). |
| 830 | 'V' cannot be greater than unity. |
| 860 | Subroutine which asks for time period since drinking began. Must be between 15 minutes and 12 hours. |
| 960 | Display message time delay sequence. |
| 940 | Sub-routine called up if negative input values are entered. |
| 980 | Warns user of fast intake rate in OPTION '1', with or without food. |

It will be noted that the user is required to input information concerning the number of drinks or drink units that he has consumed. The following is a table which is supplied with the device to assist the user in inserting the correct number of drinks, or if the calculator is so arranged the number of drink units.

TABLE

1 DRINK = 9 to 12 grams or 3/10 to 4/10 oz alcohol

| | | | |
|---|---|---|---|
| beer or cider | US | 8 oz draft | 4.2% to 5.3% |
| | UK | ½ pint | 3.7% to 5.1% |
| | US | 12 oz can | 3.7% to 4.2% |
| | AUS | 375 ml can | 3% to 4% |
| | AUS | 425 ml can | 3% |
| | UK | 440 ml can | 3.3% |
| wine | US | 3 oz glass | 12.5% to 14.5% |
| | UK/AUS | 115 ml glass | 10% to 13% |
| | UK | 130 ml glass | 10% to 11.5% |
| | US | 5 oz glass | 10.5% |
| fortified wine e.g. port, vermouth, sherry ... | UK | ¼ gill | 22% |
| | AUS | 55 ml glass | 20% |
| | US | 2 oz glass | 19% to 21% |
| distilled spirit | UK | 1/6 gill | 46% to 52% |
| | US | 1 oz glass | 45% to 50% |
| | AUS | 30 ml glass | 37% to 50% |
| | UK | 1/5 gill | 40% to 52% |
| | UK | ¼ gill | 40% |

WARNING! Home measures are often larger than you think!
Beware of what you drink at home!
Topping up glass increases alcohol intake!!!

1 UNIT = 3 grams or 1/10 oz of alcohol
Total number of UNITS to be entered must be rounded to next whole number (e.g. 7.5 to 8)

UNITED KINGDOM, EIRE

| beer | ½ pint | 440 ml | | 1 pint |
|---|---|---|---|---|
| 3.3% | 2.5 units | 4 units | | 5 units |
| 3.7% | 3 | 4.5 | | 6 |
| 4.4% | 3.5 | 5 | | 7 |
| 5.1% | 4 | 6 | | 8 |
| 5.8% | 4.5 | 7 | | 9 |
| wine | 115 ml | 130 ml | 145 ml | 170 ml |
| 10.0% | 3 units | 3.5 units | 4 units | 4.5 units |
| 11.5% | 3.5 | 4 | 4.5 | 5.5 |
| 13.0% | 4 | 4.5 | 5 | 6 |
| 14.5% | 4.5 | 5 | 5.5 | 6.5 |
| fort. wine | ¼ gill | | 95 ml | |
| 18% | 2.5 units | | 4.5 units | |
| 22% | 3 | | 5.5 | |
| dist. spirit | 1/6 gill | 1/5 gill | | ¼ gill |
| 40% | 2.5 units | 3 units | | 4 units |
| 46% | 3 | 3.5 | | 4.5 |
| 52% | 3.5 | 4 | | 5 |

U.S.A., CANADA

| beer | 8 oz | | 12 oz | |
|---|---|---|---|---|
| 3.7% | 2.5 units | | 3.5 units | |
| 4.2% | 3 | | 4 | |
| 4.7% | 3 | | 4.5 | |
| 5.3% | 3.5 | | 5 | |
| wine | 3 oz | | 5 oz | |
| 10.5% | 2.5 units | | 4 units | |
| 12.5% | 3 | | 5 | |
| 14.5% | 3.5 | | 6 | |
| fort. wine 3 oz | 19% = 4.5 units | | 21% = 5 units | |
| dist. spirit 1 oz | 45% = 3.5 units | 50% = 4 | | 55% = 4.5 |

AUSTRALIA, NEW ZEALAND

| beer | 285 ml | 375 ml | 425 ml |
|---|---|---|---|
| 2% | 1.5 units | 2 units | 2.5 units |
| 3% | 2.5 | 3 | 3.5 |
| 4% | 3 | 4 | 4.5 |
| 5% | 4 | 5 | 6 |
| wine 115 ml | 10% = 3 | 11.5% = 3.5 | 13% = 4  14.5% = 4.5 |
| fort. wine | 55 ml | dist. spirit | 30 ml |
| 17.2% | 2.5 units | 37% | 3 units |
| 20% | 3 | 50% | 4 |

What we claim is:

1. A method for limiting body alcohol concentration of a consumer, comprising the steps of:
   (a) determining the body characteristics of the consumer;
   (b) measuring the weight of the alcohol consumed (Ac) by the consumer;
   (c) measuring the time elapsed (T) during alcohol consumption;
   (d) calculating the estimated body alcohol concentration (C) as a function of the body characteristics, weight of alcohol consumed, time of consumption and
   (e) correcting said calculated concentration (C) according to whether food consumption (F) comprises (1) none, (2) a snack, or (3) a full meal, so as to obtain a corrected body alcohol concentration (Cc) by multiplying C by 1.0 if no food is consumed, by about 0.9 for a snack and by about 0.7 for a full meal; and
   (f) the consumer altering at least one of (Ac), (T) and (F) to maintain (Cc) below a predetermined maximum.

2. A method as defined in claim 1, wherein said body characteristics include weight (W), sex (S) and height.

3. A method as defined in claim 1, wherein said body characteristics include body weight (W), sex (S) and a build factor (B).

4. A method as defined in claim 1, and further comprising the step of calculating the weight of the alcohol present (Ap) in the consumer's body at any particular time in accordance with the equation $$Ap = Ac - Al$$

where (Al) is the weight of alcohol burnt up in the liver.

5. A method as defined in claim 4, wherein the estimated body alcohol concentration (C) is calculated in accordance with the equation $$C = \frac{Ap}{W \times S \times B}$$

where (W) is the consumer's body weight, (S) is the consumer's sex, and (B) is the consumer's build factor.

6. A method as defined in claim 5, and further comprising the step of calculating an estimate of the current concentration (Cc) of blood alcohol of the consumer as a function of the food (F) consumed by the consumer.

7. A method as defined in claim 1, and further comprising the steps of setting a maximum level of body alcohol concentration and sounding an alarm when the maximum is exceeded.

8. A method as defined in claim 7, and further comprising the step of calculating the quantity of alcohol that may be consumed prior to reaching said maximum level of body alcohol concentration.

9. A method as defined in claim 1, and further comprising the step of calculating a future body alcohol concentration as a function of time.

10. A method as defined in claim 1, and further comprising the step of calculating the time at which the body will reach a predetermined body alcohol concentration.

* * * * *